United States Patent [19]

Miller et al.

[11] 4,374,198

[45] * Feb. 15, 1983

[54] RAPID UTILIZATION OF DISACCEARIDES BY FERMENTATION

[75] Inventors: Franklyn D. Miller, Cincinnati, Ohio; Werner C. Muller, Dobbs Ferry, N.Y.

[73] Assignee: National Distillers & Chemical Corp., New York, N.Y.

[*] Notice: The portion of the term of this patent subsequent to Feb. 16, 1999, has been disclaimed.

[21] Appl. No.: 259,314

[22] Filed: Apr. 30, 1981

[51] Int. Cl.$^3$ .............................................. C12P 7/14
[52] U.S. Cl. .................................... 435/162; 435/813; 435/942
[58] Field of Search ............................... 435/161–165, 435/813, 940, 942

[56] References Cited

U.S. PATENT DOCUMENTS

| | | | |
|---|---|---|---|
| 2,419,960 | 5/1947 | Legg | 435/162 |
| 2,431,004 | 11/1947 | Wickerham | 435/42 |
| 4,009,075 | 2/1977 | Hoge | 435/165 X |
| 4,315,987 | 2/1982 | Muller et al. | 435/162 |

OTHER PUBLICATIONS

Cysewski et al., Biotechnology and Bioengineering, vol. XX, pp. 1421–1444 (1978).
White, J., Yeast Technology, John Wiley and Sons Inc., N.Y., 1954, pp. 334–337.
U.K. Patent Application, GB 2,036,074 A, Sep. 27, 1979.

*Primary Examiner*—Robert A. Yoncoski
*Attorney, Agent, or Firm*—Kenneth D. Tremain

[57] ABSTRACT

A feed containing a sterilie aqueous solution of fermentable sugar and minor amounts of sugar oligomers and-/or sugar repolymerizates is continuously converted by fermentation to dilute aqueous ethanol ("beer") in a series of agitated fermentation vessels employing at least two strains of yeast, the first of which provides relatively high rates of conversion of the fermentable sugar to ethanol and the second of which provides relatively high rates of conversion of the sugar oligomers and/or sugar repolymerizates to ethanol.

11 Claims, 1 Drawing Figure

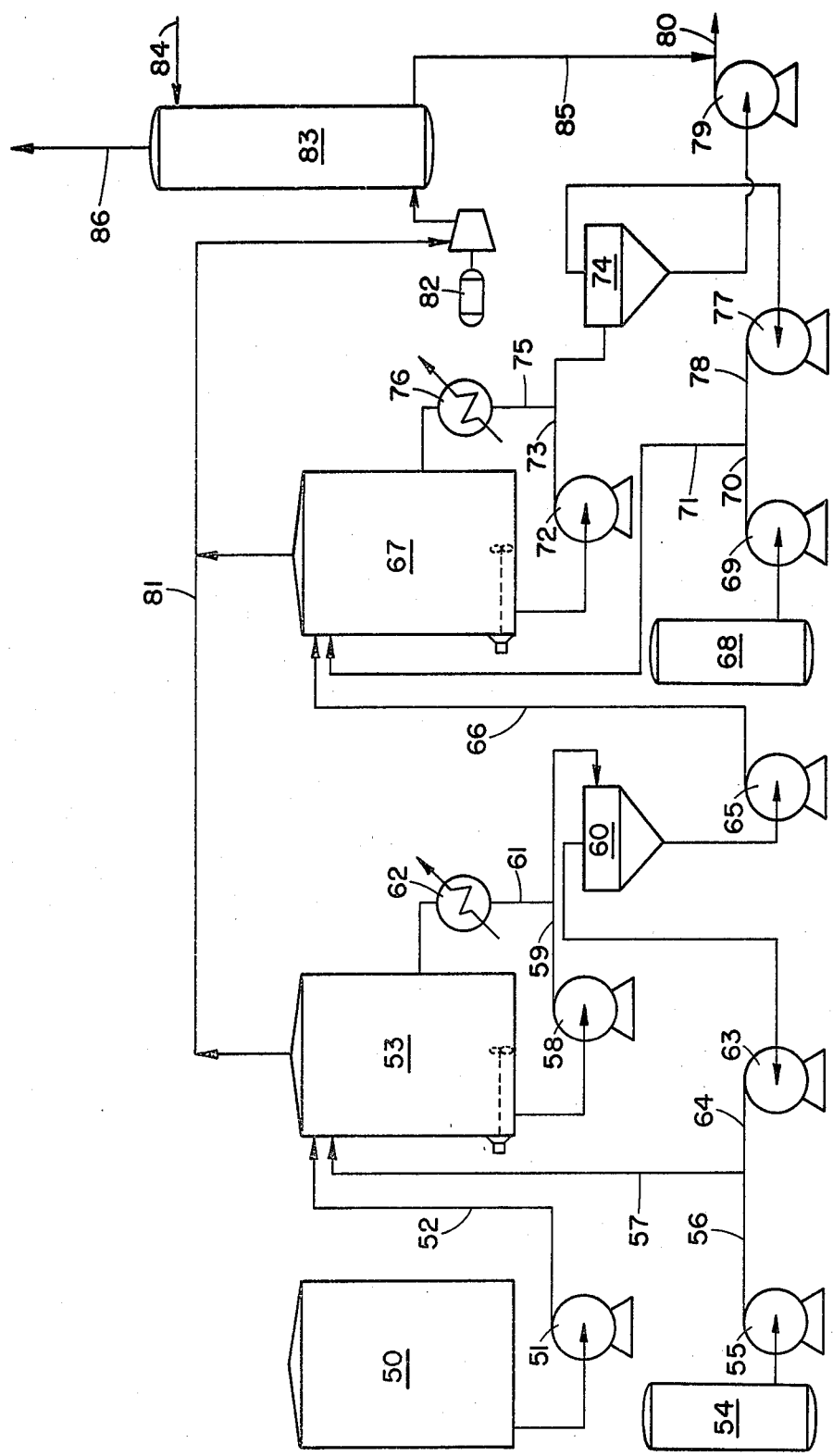

RAPID UTILIZATION OF DISACCEARIDES BY FERMENTATION

CROSS REFERENCE TO RELATED APPLICATION

This application is related to commonly assigned copending U.S. patent application Ser. No. 0,043,190, filed May 29, 1979, entitled "Fermentation Process", now U.S. Pat. No. 4,242,454.

BACKGROUND OF THE INVENTION

1. Field of the Invention

This invention relates to processes for the manufacture of ethanol by fermentation.

2. Description of the Prior Art

With the ever-increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline-10% anhydrous ethanol blend ("gasohol") has shown encouraging results. According to one study, gasohol powered automobiles have averaged a 5% reduction in fuel compared to unleaded gasoline powered vehicles and have emitted one-third less carbon monoxide than the latter. In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantities consumed and versatility.

The various operations in processes for obtaining ethanol from such recurring sources as cellulose, cane sugar and amylaceous grains and tubers, e.g., the separation of starch granules from non-carbohydrate plant matter and other extraneous substances, the chemical and/or enzymatic hydrolysis of starch to fermentable sugar (liquefaction and saccharification), the fermentation of such sugar to a dilute solution of ethanol ("beer") and the recovery of anhydrous ethanol by distillation, have been modified in numerous ways in an attempt to achieve improvements in product yield, production rates, and so forth. The substitution of alcohol for at least a portion of petroleum based fuels is particularly critical for developing economies where proven domestic petroleum reserves are limited, such as in India and Brazil, and these nations have therefore increasingly emphasized the production of alcohol from vegetative sources. However, for biomass-derived ethanol to realize its vast potential as a partial or total substitute for petroleum fuels or as a substitute chemical feedstock, it is necessary that the manufacturing process be as efficient in the consumption of raw material and energy as possible if there is to be a significant energy return for the amount of ethanol produced and if the ethanol is to become an economically viable alternative to petroleum based raw materials. To date, however, at most only modest attention has been directed to optimizing raw material and energy consumption in the manufacture of ethanol from biomass.

Processes for the continuous fermentation of sugars to provide alcohol are well known (viz., U.S. Pat. Nos. 2,155,134; 2,371,208; 2,967,107; 3,015,612; 3,078,166; 3,093,548; 3,177,005; 3,201,328; 3,207,605; 3,207,606; 3,219,319; 3,234,026; 3,413,124; 3,528,889; 3,575,813; 3,591,454; 3,705,841; 3,737,323; and 3,940,492; "Process Design and Economic Studies of Alternative Fermentation Methods for the Production of Ethanol", Cysewski, et al. *Biotechnology and Bioengineering*, Vol. xx, pp. 1421–1444 (1978)). Several known fermentation processes are known in which a combination of fermenting organisms are used (viz., U.S. Pat. Nos. 2,182,550; 2,202,785; 2,431,004; 2,419,960; 2,529,131; 2,567,257; and 3,093,548). In a typical continuous fermentation process, a stream of sterile sugar liquor and a quantity of yeast cells are introduced into the first of a battery of fermentation vessels wherein initial fermentation takes place, generally under conditions favoring rapid cell growth. The partial fermentate admixed with yeast cells is continuously withdrawn from the first fermentation vessel and introduced into a second fermentation vessel wherein fermentation is carried out under conditions favoring the rapid conversion of sugar to ethanol. The yeast in the last fermentation vessel can be recovered by suitable means, e.g., centrifugation or settlement, and recycled. It has been discovered that in such a system, the typically high concentrations of sugar which are present in the first fermentation vessel inhibit the growth and productivity of the yeast. A further drawback of conventional fermentation processes lies in their inability to effectively convert all or most of the sugar oligomers and repolymerizates to ethanol. Such oligomers and repolymerizates tend to resist conversion by yeasts which are commonly employed in known fermentation procedures. This disadvantage is particularly a problem when the sugar employed in the fermentation is derived from the acid hydrolysis of carbohydrate polymer, e.g., starch. Three of the principal types of undesirable reactions known to take place in acid catalyzed carbohydrate polymer hydrolysis are: degradation wherein the starch molecule is irreversibly destroyed to provide 5-hydroxymethylfurfural which hydrolizes to levulinic acid and formic acid, and separately to humins; reversion wherein the product glucose repolymerizes and/or isomerizes to unfermentable substances; and retrogradation wherein hydrolysis splits out the branched chain components of the starch molecule leaving a straight chain, lower molecular weight water-insoluble polymeric molecule which crystallizes at about 70°–80° C. and becomes resistant to further hydrolysis. To the extent these and other undesirable reactions take place, they cause the production of sugar derivatives which undergo fermentation to ethanol only with difficulty, if at all.

Accordingly, there has heretofore existed a need for a process of rapid, efficient continuous fermentation of fermentable sugar and sugar oligomers and/or repolymerizates such as those derived from the acid hydrolysis of starch to provide industrial ethanol at competitive prices.

SUMMARY OF THE INVENTION

In accordance with the present invention, an aqueous solution of fermentable sugar containing minor amounts of sugar oligomer and/or repolymerizate, advantageously one which has been prepared by the acid and/or enzyme hydrolysis of a carbohydrate polymer such as cellulose and/or starch, is continuously subjected to fermentation in a series of fermentation vessels in which the ethanol content of the fermentation medium is progressively increased as the sugar content of the fermentation medium is consumed by the yeast. At least two strains of yeast are selected for the fermentation, the first strain of yeast providing a relatively high rate of conversion of fermentable sugar to ethanol in a fermentation medium containing a concentration of fermentable sugar which does not significantly retard the rate of growth of the yeast, and the second strain of yeast providing a relatively high rate of conversion of the sugar oligomers and/or repolymerizates to ethanol. The process also contemplates the adjustment of temperature and/or pH in each fermentation vessel as required to maintain optimum fermentation activity therein. To conserve raw materials and direct yeast metabolic activity to the production of ethanol rather than cell growth and propagation, a portion of the yeast is continuously recycled and additional fresh yeast is added only as is necessary to replace dead cells.

The aqueous ethanol or "beer" containing as much as about 12 weight percent ethanol which is obtained by the foregoing process can be concentrated employing any of the known and conventional techniques and is advantageously concentrated by the anhydrous distillation process disclosed in commonly assigned copending U.S. patent application Ser. No. 043,189, filed May 29, 1979, entitled "Production of Anhydrous Alcohol", now U.S. Pat. No. 4,256,541. The stillage effluent obtained from the rectifying column employed in the aforesaid anhydrous distillation process contains soluble proteins and amino acids of the original beer feed and provides an excellent source of nutrient for the growth of the yeasts employed in the fermentation process herein. The stillage effluent may also contain amounts of sugar oligomers and/or repolymerizates such as to provide a useful medium for the propagation of the second strains of yeast.

The term "fermentable sugar" should be understood as referring to a single fermentable sugar such as glucose (dextrose), fructose, maltose, or sucrose but more commonly will be applicable to these and similar fermentable disaccharides in admixture. The terms "sugar oligomer" and "sugar repolymerizate" are intended to include saccharides derived from carbohydrate polymers, other than fermentable disaccharides, which do not readily undergo conversion to ethanol in the presence of a standard brewers' yeast such as *Saccharomyces cerevisiae*.

BRIEF DESCRIPTION OF THE DRAWING

The accompanying drawing is a diagrammatic flow sheet illustrative of one embodiment of an ethanol fermentation process in accordance with the present invention.

DESCRIPTION OF THE PREFERRED EMBODIMENTS

Referring to the drawing, a sterile aqueous solution of fermentable sugar from any source containing from about 10 to about 40 weight percent sugar, and preferably from about 15 to about 25 weight percent sugar, and containing minor amounts of sugar oligomers and/or repolymerizates, e.g., up to 20 weight percent of the total amount of saccharides present, is taken from vessel 50 which can be a storage vessel or a saccharification vessel in which the sugar is obtained by the hydrolysis of a carbohydrate polymer such as cellulose and/or starch, and is delivered by pump 51 through line 52 to a first temperature regulated, agitated fermentation vessel 53 provided with pH control and means for introducing nutrients and the small amounts of oxygen conventionally employed for maintaining proper yeast metabolism during fermentation. In the event the sugar solution contains more than 20 weight percent total saccharide, it is preferable to dilute the solution to about this level of saccharide, advantageously with the nitrogen-rich stillage obtained from an ethanol distillation unit such as described in the aforesaid Ser. No. 043,189, filed May 29, 1979. The use of stillage when available possesses the two-fold advantage of recycling nitrogen to the fermentation system which would otherwise be lost upon concentration of the ethanol during distillation, and reducing process water consumption by avoiding water build-up in the still bottoms. In addition to fermentable sugar, the foregoing solution may also contain significant amounts of partial hydrolysates of carbohydrate polymer (e.g., up to about 40 weight percent of the total carbohydrate present) which can be saccharified to fermentable sugar under the influence of the saccharifying enzyme produced by the fermenting yeast and/or added saccharifying enzyme. A pumpable slurry of ethanol-producing yeast organisms free of contaminating organisms is conveyed from yeast storage tank 54 by pump 55 through lines 56 and 57 into fermentation vessel 53. The yeast selected for introduction in fermentation vessel 53 is one which provides relatively high rates of conversion of fermentable sugar to ethanol. As is well known, yeasts having certain desired characteristics or functionalities can be selected or isolated employing well-defined microbiological techniques. Thus, for example, several strains of yeast can be introduced into a laboratory or large-scale fermentation vessel (e.g., a chemostat) in which initial ethanol, sugar/sugar oligomer/sugar repolymerizate and nutrient concentrations are noted and predetermined levels of temperature and pH are accurately maintained so as to simulate the conditions of a large scale fermentation unit. As the different strains of yeast compete with one another for survival over a prolonged period which can be several weeks or even months, only one or a few strains will have survived, the surviving organisms being optimal producers of ethanol under the conditions selected for the operation of the fermentation unit. Using the same procedure, the mutation of a single yeast organism to provide an optimal ethanol producer under the fermentation conditions selected can be induced. The foregoing screening procedure can also be used to evaluate and isolate selected strains of yeast produced by techniques of induced mutation, e.g., those employing ultraviolet radiation, gamma rays, etc., to accelerate the incidence of mutation. Other useful techniques for obtaining different strains of yeast for evaluation as ethanol producers under predetermined fermentation conditions include cross breeding of two different strains to yield a third and genetic engineering in which genetic materials from two different strains are recombined to form a completely new genetic "blueprint". A yeast which is known to provide especially good conversions of fermentable sugars to ethanol is the common brewers yeast *Saccharomyces cerevisiae*. The live yeast in fermentation vessels 53 and 67 can be present at a level of from about 2 to about 8 weight percent of the fermentation medium (based on dry weight of yeast) and preferably is present at from about 3 to about 6 weight percent. Once continuous fermentation has started and a steady state has been achieved, there will be no need to add more yeast other than those amounts necessary to make up for cells which die. The temperature of each fermentation vessel is advantageously regulated at a level which favors maximum ethanol production, i.e., generally from about 68° F. to about 104° F. and preferably from about 86° F. to about 99° F. The pH of each fermentation vessels is similarly regulated and can range from about 3.5 to about 5.5 and preferably from about 4.0 to 4.6. Dilute ethanol produced in fermentation vessel 53 containing a portion of the yeast cells therein is conveyed by pump 58 through line 59 to yeast separator/recovery unit 60 which separates substantially all of the yeast cells from the aqueous ethanol stream. Unit 60 can be a micro-filtration device, centrifuge, etc. Since fermentation is exothermic, a portion of the fermentation medium passing through line 59 is diverted through line 61 into cooler 62 and returned to fermentation vessel 53. The yeast cells recovered in unit 60 are conveyed as a pumpable slurry or "cream" containing from about 10 to about 50 weight percent dry yeast and preferably from about 20 to 40 weight percent dry yeast by pump 63 through lines 64 and 57 into fermentation vessel 53. The ethanol-containing fermentation medium thus freed of yeast cells is delivered by pump 65 through line 66 into fermentation vessel 67 which is essentially similar to fermentation vessel 53. A pumpable slurry of ethanol-producing yeast organisms essentially free of contaminating organisms is conveyed from yeast storage tank 68 by pump 69 through lines 70 and 71 into fermentation vessel 67. The yeast selected for introduction in fermentation vessel 67 is one which provides relatively high rates of conversion of sugar oligomers and/or repolymerizates to ethanol. Strains of yeast satisfying these requirements can be isolated in the manner described above. A yeast which is particularly well suited for this purpose is *Saccharomyces cerevisiae*, Brewery Kobenhaven #2: Peoria 6 var, ATCC No. 20610. The dilute aqueous ethanol (approximately 10 to 12 weight percent ethanol) containing yeast cells is withdrawn from fermentation vessel 67 and conveyed by pump 72 through line 73 to yeast separator/recovery unit 74. A portion of the fermentation medium passing through line 73 is diverted through line 75 into cooler 76 and returned to fermentation vessel 67. The yeast cells recovered in unit 74 are conveyed as a pumpable slurry (similar in fluid characteristics to the yeast slurry recovered from unit 60) by pump 77 through lines 78 and 71 to fermentation vessel 67. The cell-free ethanol solution from yeast separator/recovery unit 74 is delivered by pump 79 through line 80 directly to an ethanol concentration unit, e.g., anhydrous distillation apparatus, and/or to a storage facility. It is also within the scope of this invention to employ both types of yeast herein in such fermentation vessel with only one yeast separator/recovery unit (receiving the fermentation medium from the last fermentation vessel in the series) being provided. Metabolically evolved carbon dioxide gas containing ethanol is conveyed from each of fermentation vessels 53 and 67 through common line 81 and by means of blower 82 is introduced into the bottom of ethanol absorption unit 83. Water at ambient temperature entering the top of the absorption unit through line 84 and flowing downwardly absorbs substantially all of the ethanol vapor rising through the unit. The aqueous solution of ethanol withdrawn from the base of ethanol absorption unit 83 through line 85 is conveyed to line 80 where it is combined with the flow from the last fermenter. Vent gases are discharged from ethanol absorption unit 83 through atmospheric vent line 86. In yet another preferred mode, the non-converted sugars, sugar oligomers and/or sugar repolymerizates present in the still bottoms of an ethanol distillation system are effectively used as the nutrient substrate for the propagation and growth of the second yeast organism herein.

What is claimed is:

1. A process for the production of ethanol by continuous fermentation which comprises carrying out fermentation upon an aqueous solution of fermentable sugar and a minor amount of sugar oligomer and/or sugar repolymerizate in a series of fermentation vessels employing at least two different strains of ethanol-producing yeast, the first strain of yeast providing a relatively high rate of conversion of fermentable sugar to ethanol in a fermentation medium containing a concentration of fermentable sugar which does not significantly retard the rate of growth of the yeast, and the second strain providing a relatively high rate of conversion of sugar oligomers and/or sugar repolymerizates to ethanol, each of said strains of yeast being separately employed in its own fermentation vessel from which said yeast is separately recovered therefrom and recycled thereto.

2. The process of claim 1 wherein the aqueous solution of fermentable sugar contains partial starch hydrolysate in an amount of up to about 40 weight percent of the total carbohydrate present, the partial starch hydrolysate undergoing saccharification to fermentable sugar under the influence of saccharifying enzyme produced by the yeast and/or added saccharifying enzyme.

3. The process of claim 1 wherein the strain of yeast which provides a relatively high rate of conversion of fermentable sugar to ethanol is *Saccharomyces cerevisiae*.

4. The process of claim 1 wherein the strain of yeast which provides a relatively high rate of conversion of sugar oligomers and/or sugar repolymerizates to ethanol is *Saccharomyces cerevisiae*, Brewery Kobenhaven #2: Peoria 6 var.

5. The process of claim 1 wherein ethanol contained in the carbon dioxide gas evolved during fermentation is recovered.

6. The process of claim 1 wherein from 2 to 8 weight percent of yeast calculated on a dry yeast basis is present in each fermentation vessel.

7. The process of claim 6 wherein from 3 to 6 weight percent of yeast calculated on a dry yeast basis is present in each fermentation vessel.

8. The process of claim 1 wherein the aqueous solution of fermentable sugar contains from about 10 to about 40 weight percent sugar.

9. The process of claim 8 wherein the aqueous solution of fermentable sugar contains from about 15 to 25 weight percent sugar.

10. The process of claim 1 wherein the aqueous solution contains up to about 20 weight percent of sugar oligomers and/or repolymerizates based on the total weight of saccharide present.

11. The process of claim 1 wherein stillage effluent containing sugar oligomers and/or repolymerizates is utilized as a nutrient medium for the propagation and/or growth of the second strain of yeast.

* * * * *